US00RE36583E

United States Patent [19]

Pomatto et al.

[11] E Patent Number: Re. 36,583

[45] Reissued Date of Patent: Feb. 22, 2000

[54] CRANIAL REMODELING ORTHOSIS

[76] Inventors: R. Craig Pomatto, 6633 E. Greenway Pky. #1035, Scottsdale, Ariz. 85254; Jeanne K. Pomatto, 7665 Larkspar Dr., Scottsdale, Ariz. 85260

[21] Appl. No.: 08/876,682

[22] Filed: Jun. 16, 1997

Related U.S. Patent Documents

Reissue of:

[64] Patent No.: 5,308,312
Issued: May 3, 1994
Appl. No.: 08/026,774
Filed: Mar. 5, 1993

U.S. Applications:

[63] Continuation of application No. 08/467,594, Jun. 6, 1995, abandoned.

[51] Int. Cl.[7] ..... A61F 5/00

[52] U.S. Cl. ..... 602/17; 602/6

[58] Field of Search ..... 602/5–8, 17; 2/411, 2/412, 414

[56] References Cited

U.S. PATENT DOCUMENTS

| | | | |
|---|---|---|---|
| 1,569,181 | 1/1926 | Hartman | 2/414 |
| 1,576,987 | 3/1926 | Mullins | 2/414 |
| 2,758,304 | 8/1956 | McGowan | 2/411 |
| 3,364,499 | 1/1968 | Kwoka | 2/414 |
| 3,577,562 | 5/1971 | Holt | 2/414 |
| 4,352,352 | 10/1982 | Janovsky et al. | 602/17 |
| 4,377,009 | 3/1983 | Douglas | 2/411 |
| 4,645,198 | 2/1987 | Levenston . | |
| 4,722,056 | 1/1988 | Roberts et al. | 364/413 |
| 4,742,464 | 5/1988 | Duret et al. | 364/474 |
| 4,776,324 | 10/1988 | Clarren | 602/17 |
| 4,821,200 | 4/1989 | Oberg | 364/474.24 |
| 5,094,229 | 3/1992 | Pomatto et al. | 602/17 |
| 5,119,516 | 6/1992 | Broersma | 2/412 X |
| 5,177,815 | 1/1993 | Andujar | 2/411 |

FOREIGN PATENT DOCUMENTS

| | | | |
|---|---|---|---|
| 2509585 | 1/1983 | France | 2/411 |
| 0659134 | 4/1979 | U.S.S.R. | 2/412 |

*Primary Examiner*—Richard J. Apley
*Assistant Examiner*—Denise Pothier
*Attorney, Agent, or Firm*—Donald J. Lenkszus; Bryan Cave, LLP

[57] ABSTRACT

A cranial remodeling orthosis is shaped to extend across the top of the head with depending regions closely confining the temporal bone regions and the mastoid process regions of the cranium. The orthosis is self-suspending and preferably includes an elastic band for imparting ear-to-ear rigidity to the device.

35 Claims, 1 Drawing Sheet

CRANIAL REMODELING ORTHOSIS

Matter enclosed in heavy brackets [ ] appears in the original patent but forms no part of this reissue specification; matter printed in italics indicates the additions made by reissue.

*This application is a continuation of Ser. No. 08/467,594, filed Jun. 6, 1995, abandoned.*

TECHNICAL FIELD

This invention is concerned with correcting brachycephalic cranial abnormalities in humans.

BACKGROUND ART

Otherwise normal children may be afflicted with cranial abnormalities, known as plagiocephaly, which also contribute to facial asymmetry. Such abnormalities are correctable, particularly if treatment is undertaken at an early age, preferably when the subject is less than six months old. The subject can thus be spared the indignity of going through life with a cosmetic disability.

In U.S. Pat. No. 5,094,229, granted Mar. 10, 1992, for "CRANIAL REMODELING ORTHOSIS", the present applicants discuss different approaches to cranial remodeling and disclose an improved cranial remodeling band for correcting plagiocephaly. Reference is made to the patent for further background art for the present invention.

The band orthosis of the '229 patent is effective for treatment of a variety of cranial abnormalities. However, it is believed that one particular form of abnormality can be corrected with somewhat different orthosis design and treatment methodology. This abnormality is known as brachycephalic cranial head shape abnormality. The brachycephalic head shape expresses itself as occipital flattening of the cranium with resultant biparietal breadth and/or height abnormalities usually accompanied by bi-temporal and frontal breadth abnormalities. The supernormal brachycephalic head shape is one in which the maximum cranial breadth departs from established anthropometric norms in being disproportionately large in relation to the maximum cranial length.

DISCLOSURE OF THE INVENTION

The orthosis of this invention acts to correct brachycephaly by constraining growth across the breadth and height of the cranium while encouraging an increase in the maximum cranial length. The orthosis is configured to extend across the top of a head with depending regions closely confining the temporal bone regions and the mastoid process regions of the cranium. The orthosis is self-suspending and preferably includes an elastic band for imparting ear-to-ear rigidity to the device.

BRIEF DESCRIPTION OF THE DRAWINGS

This invention is described in greater detail hereinafter by reference to the accompanying drawings wherein.

BEST MODE FOR CARRYING OUT THE INVENTION

Figure 1:
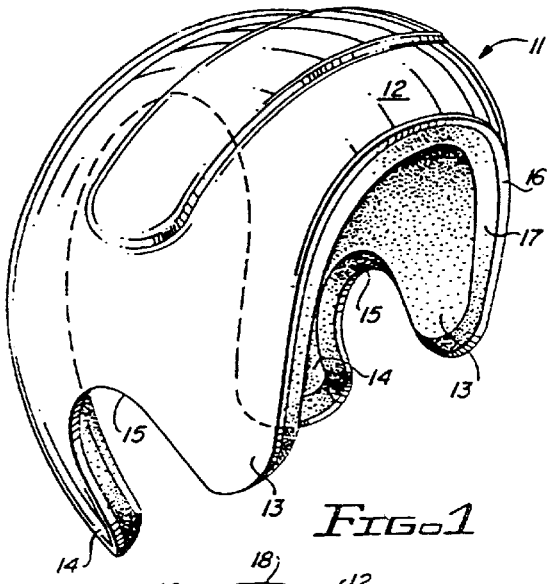
FIG. 1 is a perspective view of an orthosis constructed in accordance with this invention.
Figure 2:
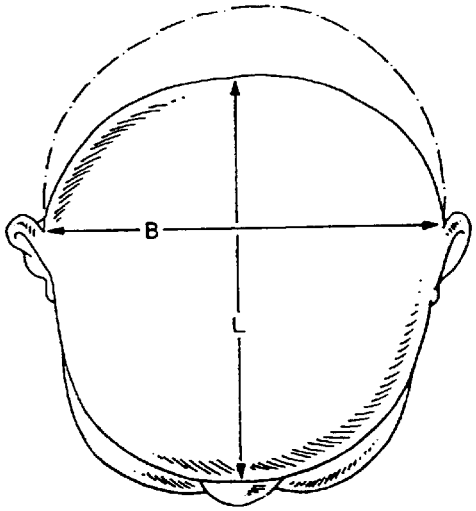
FIG. 2 is a view of the top of an infant's head, illustrating the abnormality known as brachycephaly.

In the drawing, the numeral 11 is employed to indicate, generally, the orthosis of this invention. This orthosis is employed to correct the cranial abnormality known as "brachycephaly" which is illustrated in FIG. 2. Referring specifically to FIG. 2, the abnormality is manifested as a cranial condition in which the breadth "B" of the cranium is disproportionately large in relation to the length "L" of the cranium. The orthosis 11 is employed to remodel the cranium by allowing growth of the cranium length to the dot and dash configuration shown while constraining growth of the cranium in breadth.

Figure 3:
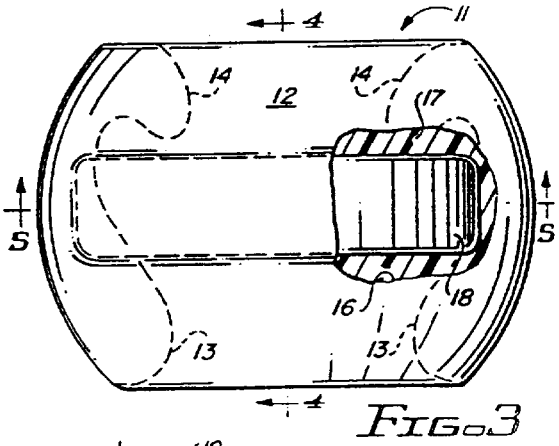
FIG. 3 is a top view of the orthosis with a portion broken away to show its construction.
Figure 4:
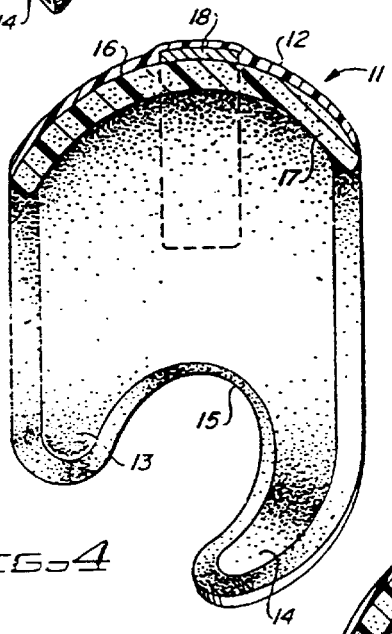
FIG. 4 is a sectional view from the side of the orthosis, taken as indicated, by line 4—4 in FIG. 3.
Figure 5:
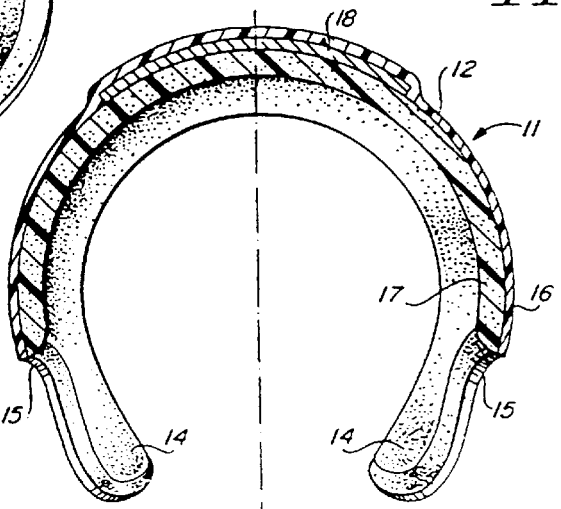
FIG. 5 is a sectional view of the orthosis taken as indicated by line 5—5 in FIG. 3.
Figure 6:
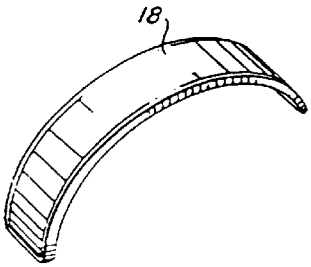
FIG. 6 is a perspective view of an elastic band employed in the orthosis.

The preferred configuration for the orthosis is illustrated in FIGS. 3–5. It comprises a central, or upper, region 12 which is shaped to extend over the top and closely conform to the configuration of the top of the cranium. For most subjects, this region 12 of the orthosis will cover an anterior region of the parietal bone and possibly a posterior region of the frontal bone. Depending upon the size of the cranium of the subject, this upper region 12 of the orthosis will have a front to back width of approximately four (4) to five (5) inches (10.16 to 12.7 cm.).

Integrally associated with the central region 12 of the orthosis are depending regions 13 and 14 on each side of the orthosis. Depending regions 13 are shaped to closely confine temporal bone regions of the cranium adjacent and forward of the ears of the subject. Depending regions 14 are shaped to closely confine mastoid process regions of the cranium to the rear and beneath the ears of the subject. Cut out regions 15 between depending regions 13 and 14 uncover the ears of the subject for his or her comfort.

It is important that the orthosis 11 be configured to be self-suspending, i.e., remain in stabilized position on the cranium of the subject without the aid of a chin strap. The latter aid, which is often required with helmet-type orthosis, is deemed undesirable because it can interfere with eating and possibly deform the subject's jaw bone.

Self-suspension of the orthosis 11 of this invention is achieved as a result of the close confinement of the temporal bone and mastoid process regions of the cranium by the depending regions 12 and 13 of the orthosis. The regions of contact formed by orthosis regions 12 and 13 fall within planes of the cranium which have circumferences which are less than the maximum occipitofrontal circumference of the subject's cranium. The inherent resiliency of the orthosis (which is discussed hereafter) draws the orthosis down with the central region 12 in contact with the top of the subject's head and holds the orthosis in place.

Orthosis 11 is constructed with an outer layer 16 of plastic material and an inner liner 17 of compressible foam material. For most infant and child orthoses, sheet plastic of co-polymer polypropylene material approximately 3/16" (4.76 mm) thick is suitable for forming the outer layer 16. This material is light in weight, possesses considerable strength, yet is resilient and is thermoformable to almost any desired shape. The preferred material for the liner 17 is sheet polyurethane foam having a thickness of approximately 3/8" (10 mm).

For treating many subjects, the inherent stiffness and resiliency of the outer layer 16 of polypropylene will be sufficient to hold the orthosis in place and effectively restrain growth across the breadth and height of the cranium. However, if desired, the ear-to-ear stiffness of the orthosis can be enhanced by incorporating stiffening means therein, preferably in the form of an arcuate elastic band 18 positioned in the upper region 12 of the orthosis. A carbon fiber material is preferred for the band 18 inasmuch as this material offers significant strength with very little weight. For the comfort of the subject, it is desirable to keep the weight of the orthosis as low as possible.

It can be appreciated that the orthosis 11 must be constructed to afford some flexibility to permit the opposite depending regions 13 and 14 to be spread apart to install and remove the orthosis from the subject's head.

For maximum effectiveness, the orthosis of this invention should be individualized for each subject. This means that each orthosis should be fabricated from an impression of the head of the subject of be treated.

The technique for fabricating an orthosis 11 involves forming a positive model of the subject's skull. This model can be constructed from a plaster of Paris negative mold of the head or from a digitized laser image of the head. The positive model is modified to the configuration desired for the remodeled cranium and then employed to shape the orthosis. The latter step involves draping the liner material 17 over the model and then vacuum thermoforming the outer layer material 16 over the model. The model is removed from this structure and the structure is trimmed to the configuration illustrated in the drawing and described above. If the elastic band 18 is to be employed, it is pre-shaped to the desired configuration and placed over the liner material 17 before the outer layer material 16 is thermoformed. This encases the band 18 between outer layer 16 and liner 17.

We claim:

1. A cranial remodeling orthosis comprising a resilient band adapted to extend across the parietal bone region of the cranium and having depending regions shaped to closely confine the temporal bone regions and the mastoid process regions of the cranium with relief areas therebetween to expose the ears of a patient wearing the orthosis, said depending regions of the orthosis being adapted to provide regions of contact which fall within planes of the cranium which have circumferences which are less than the maximum occipitofrontal circumference of the cranium whereby the orthosis is held in place on the cranium.

2. The orthosis of claim 1, further comprising, rigidity imparting means in the form of an elastic band within that portion of the orthosis band which is adapted to extend across the parietal region of the cranium.

3. The orthosis of claim 2, wherein said elastic band is formed from a carbon fiber material.

4. The orthosis of claim 2, further characterized in that said orthosis comprises an outer layer of thermoformed plastic material and an inner liner of cushioning material and said elastic band is disposed between said outer layer and said inner liner.

*5. A method for fabricating a cranial remodeling orthosis for a patient having a condition known as brachycephalic cranial head shape abnormality, said method comprising the steps of:*

*forming a negative impression of the head of said patient;*

*forming a positive impression from said negative impression;*

*modifying said positive impression to a desired corrected shape of said patient's head;*

*utilizing said modified impression to produce said orthosis;*

*configuring said orthosis to correct brachycephaly by constraining growth across the breadth and height of the cranium of said patient and permitting growth in the direction of the length of said cranium.*

*6. A method in accordance with claim 5, comprising the step of:*

*forming said orthosis to have portions shaped to closely confine the temporal bone regions and mastoid process regions of said cranium to restrict growth.*

*7. A method in accordance with claim 6, comprising the step of:*

*forming said orthosis to be self-suspending on said patient's head without the use of strap devices.*

*8. A method in accordance with claim 7, comprising the step of:*

*forming said orthosis to include relief areas to expose the ears of said patient.*

*9. A method in accordance with claim 5, comprising the step of:*

*forming said orthosis to include relief areas to expose the ears of said patient.*

*10. A method in accordance with claim 5, comprising the step of:*

*forming said orthosis to be self-suspending on said patient's head without the use of strap devices.*

*11. A method in accordance with claim 10, comprising the step of:*

*forming said orthosis from a resilient material.*

*12. A method in accordance with claim 11, comprising the step of:*

*forming said orthosis of polypropylene material.*

*13. A method in accordance with claim 5, comprising the step of:*

*selecting a resilient material to be included in the construction of said orthosis.*

*14. A method in accordance with claim 13, comprising the step of:*

*forming said orthosis such that said orthosis has a resilient property which causes said orthosis to be urged into contact with said patient's head and holds said orthosis in place.*

*15. A method in accordance with claim 5, comprising the steps of:*

*conforming a liner material to said modified impression; and*

*forming an outer material over said liner material to form a resilient band.*

*16. A method in accordance with claim 15, comprising the step of:*

*positioning one stiffening member in a predetermined position between said liner material and said outer layer material.*

*17. A method in accordance with claim 5, comprising the steps of:*

*draping a liner material over said modified impression; and*

*vacuum thermoforming an outer layer material over said liner material to form a resilient band.*

*18. A method in accordance with claim 17, comprising the step of:*

*trimming said resilient band to a desired configuration.*

*19. A method in accordance with claim 17, comprising the step of:*

*positioning at least one stiffening member in a predetermined position on said liner material prior to said vacuum thermoforming.*

*20. A method in accordance with claim 19, comprising the step of:*

*said stiffening member is preshaped to a desired shape.*

*21. A method for fabricating a cranial remodeling orthosis comprising the steps of:*

*forming a negative impression of the head of a patient;*

*forming a first positive mold of said patient's head;*

*forming a second positive mold by modifying said first positive mold to a desired shape of said patient's head; and*

*forming a resilient band, said resilient band being shaped to extend across the parietal bone region of the cranium of said patient and having depending regions shaped to closely confine the temporal bone regions and mastoid process regions of said cranium.*

*22. A method in accordance with claim 21, comprising the step of:*

*shaping said resilient band with relief areas to expose the ears of said patient.*

*23. A method in accordance with claim 21, comprising the step of:*

*adapting said resilient band to provide regions of contact with the temporal bone areas and mastoid process areas of said patient's cranium, said regions falling within planes of said cranium which have circumferences which are less than the maximum occipitofrontal circumference of said cranium.*

*24. A method in accordance with claim 23, comprising the step of:*

*adapting said resilient band to draw said orthosis down to contact the top of said patient's head and thereby hold said orthosis in place.*

*25. A method in accordance with claim 21, comprising the steps of:*

*conforming a liner material to said second positive mold; and*

*forming an outer material over said liner material to form said resilient band.*

*26. A method in accordance with claim 21, comprising the steps of:*

*draping a liner material over said second positive mold; and*

*vacuum thermoforming an outer layer material over said liner material to form said resilient band.*

*27. A method in accordance with claim 25, comprising the step of:*

*positioning one stiffening member in a predetermined position between said liner material and said outer layer material.*

*28. A method in accordance with claim 26, comprising the step of:*

*trimming said resilient band to a desired configuration.*

*29. A method in accordance with claim 26, comprising the step of:*

*positioning at least one stiffening member in a predetermined position on said liner material prior to said vacuum thermoforming.*

*30. A method in accordance with claim 29, wherein:*

*said stiffening member is preshaped to a desired shape.*

*31. A method for producing a cranial remodeling orthosis for a patient comprising the steps of:*

*providing a digitized three-dimensional image of said patient's head;*

*producing a cranial remodeling orthosis from said digitized image;*

*forming a resilient band shaped to directionally restrict growth of said patient's cranium to correct a brachycephalic cranial head shape abnormality of said patient; and*

*shaping said resilient band to extend across the parietal bone region of said patient's cranium and having depending regions shaped to closely confine the temporal bone regions and mastoid process regions of said patient's cranium.*

*32. A method for producing a cranial remodeling orthosis for a patient comprising the steps of:*

*providing a digitized three-dimensional image of said patient's head;*

*producing a cranial remodeling orthosis from said digitized image;*

*producing a positive image of said patient's head from said digitized image;*

*modifying said positive image to a desired shape for the cranium of said patient;*

*conforming a liner material to said modified positive image;*

*forming an outer material over said liner material to form said orthosis; and*

*positioning one stiffening member in a predetermined position between said liner material and said outer material.*

*33. A method in accordance with claim 32, comprising the step of:*

*trimming said resilient band to a desired configuration.*

*34. A method in accordance with claim 33, wherein:*

*said stiffening member is preshaped to a desired shape.*

*35. A method in accordance with claim 32, comprising the additional step of:*

*positioning at least one stiffening member in a predetermined position on said liner material prior to said vacuum thermoforming.*

* * * * *